United States Patent [19]
Baust et al.

[11] Patent Number: 5,254,116
[45] Date of Patent: Oct. 19, 1993

[54] CRYOSURGICAL INSTRUMENT WITH VENT HOLES AND METHOD USING SAME

[75] Inventors: John G. Baust, Candor; ZhaoHua Chang, Binghamton, both of N.Y.; J. J. Finkelstein, Bethesda, Md.

[73] Assignee: Cryomedical Sciences, Inc., Rockville, Md.

[21] Appl. No.: 756,287

[22] Filed: Sep. 6, 1991

[51] Int. Cl.$^5$ .............................................. A61B 17/38
[52] U.S. Cl. ...................................... 606/23; 606/21; 607/105
[58] Field of Search ....................... 606/20, 21, 22, 23; 128/399, 400, 401

[56] References Cited

U.S. PATENT DOCUMENTS

| | | | |
|---|---|---|---|
| 3,333,587 | 8/1967 | Johnston | 606/23 |
| 3,369,550 | 2/1968 | Armao | 606/20 X |
| 3,662,755 | 5/1972 | Rautenbach et al. | 606/24 |
| 3,907,339 | 9/1975 | Stumpf et al. | 606/20 X |
| 4,211,086 | 7/1980 | Leonard et al. | 128/201.21 X |
| 5,100,425 | 3/1992 | Fischell et al. | 604/22 X |

FOREIGN PATENT DOCUMENTS

| | | | |
|---|---|---|---|
| 0808081 | 2/1981 | U.S.S.R. | 606/21 |
| 1153901 | 5/1985 | U.S.S.R. | 606/23 |

Primary Examiner—Stephen C. Pellegrino
Assistant Examiner—Jeffrey A. Schmidt
Attorney, Agent, or Firm—Sherman and Shalloway

[57] ABSTRACT

A closed end surgical cryoprobe instrument with probe shaft diameter of 3 millimeters or less is made to achieve and maintain freezing zone temperatures close to that of the liquid cryogenic refrigerant. Using sub-cooled liquid nitrogen at approximately −208° C. freezing zone temperatures as low as −206° C. can be achieved in under 1 minute. The liquid nitrogen supply tube is provided with a plurality of small vent holes to vent gas formed or present in the refrigerant supply tube to the return refrigerant flow channel. The vent holes also allow small amount of liquid nitrogen to vent into the return flow channel to further reduce the temperature differential between the sub-cooled liquid nitrogen supply and the counter-current flowing return refrigerant.

24 Claims, 1 Drawing Sheet

CRYOSURGICAL INSTRUMENT WITH VENT HOLES AND METHOD USING SAME

FIELD OF THE INVENTION

This invention relates to a cryosurgical instrument suitable for use in destroying living tissues, such as solid malignant or benign tumors. More particularly, the invention relates to a surgical cryoprobe instrument capable of rapidly producing very low temperatures and maintaining very low temperatures even under heat conditions, such as, when surrounded by tissue and which is highly effective in the surgical treatment of various disorders, especially in destroying tumors. Even more specifically, the invention relates to a surgical cryoprobe with means for quickly producing at the probe tip temperatures below the melting temperature of tissue ($-0.57°$ C.) and maintaining very low temperatures, using liquid nitrogen as the coolant, which coolant temperatures can be lower than the normal boiling temperature of nitrogen. The invention specifically relates to such cryoprobe instruments which have ventilation holes in the liquid nitrogen delivery tube, strategically positioned to vent gas formed in the liquid nitrogen delivery tube into the exhaust tube before the gas reaches the tip of the cryoprobe.

DISCUSSION OF THE PRIOR ART

Cryosurgical probes are used in a wide variety of surgical procedures including removal of cataracts, repairing detached retinas, treating cervicitis, cervical erosion, removal of cysts, etc. Until very recently, cryosurgery has been applied primarily to the outer surface of the body. However recent advances in cryosurgery have enabled its application to the removal of unwanted tissue deep in the body. These advances include the coupling of imaging techniques, such as ultrasound or magnetic resonance imaging with cryosurgery so that the extent of the tumors, as well as that of the frozen tissue can be readily ascertained. Moreover, Rubinsky and Pegg, Proc. R. Soc. Lond. B324, 343-358 (1988) have shown that the process of freezing in tissue and the ultimate destruction of frozen tissue is preceded by destruction of the vasculature network surrounding the tissue. It thus appears that the destruction of the frozen tissue is promoted by the lack of blood supply to the frozen tissue after thawing. Consequently, the thawed tissue is destroyed by ischemic necrosis. These authors also showed that tissue at the outer edges of the frozen region is most readily destroyed.

Most conventional cryoprobe instruments operate with liquid nitrogen ($LN_2$) or other liquified gas as the cooling medium. The $LN_2$ is introduced into the freezing zone of the probe through a feed or delivery tube, which is usually the innermost tube of three concentric tubes. The delivery tube extends into an expansion chamber at the closed probe tip end but terminates a distance from the tip. The $LN_2$ rapidly vaporizes and expands about 700-fold in volume. As the liquid vaporizes, it absorbs heat from the probe tip to lower its temperature, theoretically to the normal boiling point of $LN_2$ (about $-196°$ C. at 1 atmosphere). When the cryoprobe is placed in contact with the tumor tissue, however, a nitrogen gas pocket inevitably forms close to the inner surface of the tip, which retards the liquid flow and consequently decreases the heat transfer efficiency. The returning nitrogen gas further warms the liquid nitrogen in the supply tube, making it more difficult to achieve low temperature in the probe tip. To avoid this cascading blockage and maintain a steady flow of $LN_2$ to the tip, conventional cryoprobes must be rapidly vented, which requires a large returning space and therefore a large overall diameter of the probe.

In addition, at start up of the surgical procedure with the cryoprobe tip placed in or on the diseased tissue, the heat load on the probe is especially high and long time periods are required to cool the probe tip to its lowest operating temperature. In practice, with conventional cryoprobes and using liquid nitrogen as the cryogenic refrigerant, the lowest tip temperatures are rarely below $-160°$ C.

However, lower temperatures can provide higher efficiency in tissue destruction by freezing larger areas with the same probe tip size or surface area. It is desirable to keep the diameter of the probe tip as small as possible to afford accuracy and control to the user, but this is complicated by the need to have a free flow of $LN_2$.

Because of the use of vaporization of $LN_2$ at the probe tip end to achieve cooling, liquid nitrogen has previously been considered to be suitable only for large cryoprobes, e.g. cryoprobes having probe tips having an outer diameter larger than 3 mm. For miniature cryoprobes cold nitrogen gas or helium gas is often used instead of liquid nitrogen. This compromise has proven unsatisfactory because the heat transfer efficiency between the gas and the probe tip in contact with the tissue is very low and consequently, the ice ball created at the tip is not large enough and the temperature is not low enough for typical clinical applications. Moreover, the pressure used for such probes is often in excess of 500 or 600 psi, which requires special safeguards to prevent potential hazards.

Vaporization of $LN_2$ within the supply tube leading to the probe tip has previously caused considerable problems for large, as well as smaller cryoprobes. Vaporization of $LN_2$ within the supply tube is probably due in part, to warming of the liquid nitrogen by the surrounding exhaust nitrogen gas returning from the tip. That is, because the exhaust gas is warmer than the $LN_2$ in the supply tube, there is counter-current heat exchange and the temperature of $LN_2$ in the supply tube is increased, resulting in further gas formation in the supply $LN_2$. This warming of the liquid nitrogen within the supply tube causes $LN_2$ to vaporize, forming nitrogen gas bubbles which impede the flow of $LN_2$ to the tip. Furthermore, warming of $LN_2$ in the supply tube by exhaust gas results in considerable delay in achieving the required temperature at the probe tip.

To some extent, these problems were solved in the cryosurgical probe and system disclosed in the commonly assigned, copending application Ser. No. 07/588,329, filed Sep. 26, 1990 in the name of B. Rubinsky, et al. Among other advantageous features disclosed in this prior application, the cryosurgical probe was designed to use sub-cooled liquid nitrogen for cooling the probe tip in the freezing zone, thereby enabling to achieve tip temperatures as low as $-196°$ C. or below, without requiring evaporative cooling in the "expansion" chamber of the closed probe tip end. Consequently, the return nitrogen cryogen in the exhaust tube can be maintained at a lower temperature than in conventional cryoprobes operating on the evaporative cooling principle. However, in practice, relatively long initial start-up times were still required to achieve the very low operating temperature at the tip. For example, even with high flow rates of the sub-cooled $LN_2$ it would take as long as 20 minutes or more for the probe tip temperature to drop to $-196°$ C. or below. These long start-up periods, needless to say, could be quite inconvenient during surgery.

The present inventors have now discovered a solution to this problem which remarkably reduces the time required to lower the probe tip temperature in the freezing zone to below $-196°$ C. to as little as 60 seconds or less.

Accordingly, an object of this invention is to provide a cryosurgical probe device which can achieve high heat transfer efficiency in a miniature probe by directing sub-cooled liquid nitrogen to the probe tip under conditions which reduce vaporization of the refrigerant at the probe tip and in the refrigerant return line.

Another object of this invention is to provide a cryosurgical probe device which provides venting of gasified coolant in the transporting hose before the gas flows into the probe supply tube and thus maintain a high flow rate of liquid nitrogen through the probe supply tube.

Still another object of this invention is to provide a cryosurgical probe device wherein the extent of counter-current heat exchange in the cryogen supply tube is decreased by venting a small volume (e.g. drops) of liquid nitrogen through holes provided along the supply tube. A related and more specific object is to provide a cryosurgical probe instrument which allows small volumes (e.g. drops) of liquid cryogen to pass through vent holes in the cryogen supply tube and vaporize in the cryogen return tube resulting in a liquid to gas phase transition in the return tube which causes Joule-Thomson cooling of the liquid cryogen flowing through the cryogen supply tube.

Still yet another object of this invention is to provide a small, lightweight, and relatively inexpensive cryoprobe which can achieve greater and more efficient freezing for any given probe tip diameter than in presently available cryoprobes.

A further and principle object of this invention is to provide a cryosurgical probe device which requires a shortened period of time to cool the probe tip to the desired low temperature.

Yet another object of the invention is to provide a cryosurgical probe device capable of achieving and maintaining temperatures below $-196°$ C.

Another and related object is to provide a cryosurgical probe instrument and system in which all components required for effectively performing a cryosurgical procedure are contained within a compact movable unit.

Still yet another object of the invention is to provide a cryosurgical system capable of operating at lower pressure.

SUMMARY OF THE INVENTION

The above and other objects of the invention which will become more apparent from the following detailed description and accompanying drawing are, in part, provided by a cryosurgical instrument having a hollow probe tip having a closed end forming a freezing zone for freezing live tissue, the instrument including a first inlet for receiving cryogenic liquid refrigerant and a first outlet for removing cryogenic refrigerant, a refrigerant supply tube for transporting cryogenic liquid refrigerant from the first inlet to the probe tip, the supply tube having at least one longitudinally located ventilation hole of a size sufficiently small to prevent the free flow of refrigerant therethrough yet providing the ventilation of any gas present in the supply tube, an exhaust flow tube for transporting refrigerant to the first outlet, wherein the supply tube and exhaust flow tube are arranged as concentric inner and outer tubes, with the supply tube forming the inner tube and extending beyond the outer tube in the freezing zone, and a thermal insulation chamber surrounding the concentric supply and exhaust tubes and extending to the freezing zone. The ventilation hole(s) allow any gas formed or present in the supply tube to vent into the exhaust tube so as to maintain a high flow rate of refrigerant through the supply tube. The vent hole(s) also function to decrease the extent of counter-current heat exchange between the supply $LN_2$ return coolant by allowing refrigerant droplets to vent into the exhaust flow tube and thereby reduce the temperature differential between the supply tube and the exhaust tube by further lowering the refrigerant temperature in the exhaust tube. Preferably, the exhaust tube is enlarged at the proximal end of the probe (corresponding to the handle portion, upstream from the freezing zone at the closed probe tip end) to promote unimpeded flow of the exhaust refrigerant. The supply tube will preferably have a first ventilation hole located in a region of the supply tube surrounded by this enlarged area of the exhaust tube. The supply tube preferably includes a plurality of ventilation holes located longitudinally and downstream from the first ventilation hole, and which may be of smaller diameter than the first ventilation hole In a preferred embodiment, the supply tube has an upstream region (including at least the freezing zone) and downstream region (corresponding to at least the handle portion) relative to the distal or closed end of the probe tip, the latter having a larger diameter than the former, thereby further promoting the rapid and unimpeded flow of the supply coolant to the freezing zone and allowing a smaller outside diameter in the region of the probe (e.g. probe shaft and tip) actually required for surgery.

In yet another embodiment, the exhaust flow tube similarly has an upstream region (including at least the freezing zone, and preferably the probe shaft), a first downstream region generally located in the probe handle and having a larger diameter than the upstream region, and a second downstream region at the exhaust outlet which forms an enlarged chamber having an outer diameter larger than that of the first downstream region. In another embodiment, the upstream area of the exhaust flow tube in the probe shaft includes means to prevent contact between the wall of the exhaust tube and the outer probe shell whereby the formation of ice crystals in the upstream region area is inhibited.

In a preferred embodiment, the thermal insulation chamber is a closed vacuum chamber which has a plurality of gas absorbing particles which may be adhered to the inner surface thereof, to further reduce and maintain a high vacuum.

DETAILED DESCRIPTION OF THE INVENTION

Figure 1:
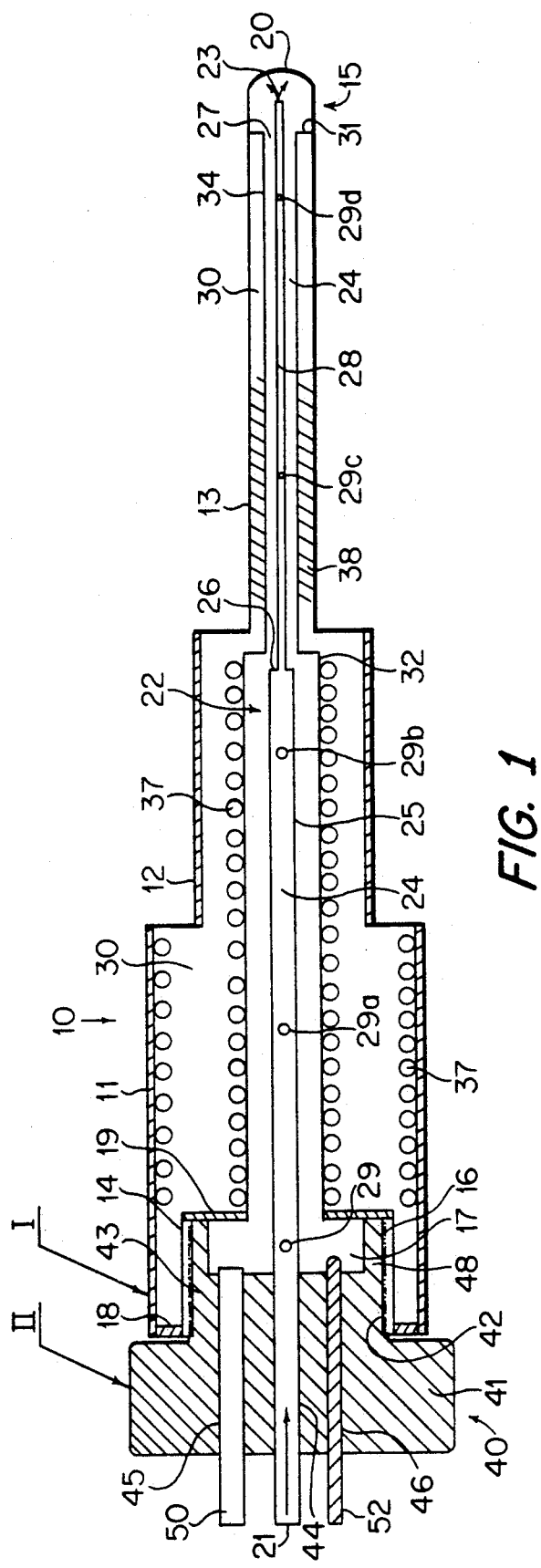
FIG. 1 is a sectional side view of one embodiment of the present invention.

The cryosurgical instrument of the present invention is a relatively small diameter cryosurgical probe of the type used to treat living tissue such as solid benign or malignant tumors. The cryosurgical instrument or cryoprobe may be of the same general construction and incorporate any or all of the features disclosed in the aforementioned Rubinsky, et al application Ser. No. 07/588,329, the disclosure of which is incorporated herein by reference thereto. The cryosurgical instrument is cooled by a liquid refrigerant, such as, liquid nitrogen, however, other liquid refrigerants capable of generating subfreezing temperatures, especially below −60° C., can also be used to cool the probe. Examples of such cryogenic liquids include, for example, freon 12, freon 22, freon 13, liquefied air and liquefied normally gaseous hydrocarbons.

However, to achieve the full advantages of the surgical cryoprobe of the present invention, the liquid nitrogen refrigerant will be sub-cooled to a temperature below its normal boiling point (−195.8° C.) and generally above its normal freezing point (−210° C). In general, the sub-cooled refrigerant will be cooled to a temperature ranging from about −198° C. to −210° C., preferably, from about −200° to −208° C., especially about −208° C., in the refrigeration system in which sub-cooling occurs. Therefore, by maintaining appropriate flow rates and sufficient thermal insulation, the sub-cooled liquid nitrogen ca be delivered to the closed end of the probe tip at operating temperatures below the normal boiling point of liquid nitrogen, ($LN_2$), below −196° C., and especially about −206° C.. Furthermore, using the invention cryoprobe to deliver sub-cooled cryogenic liquid, it becomes possible to lower the temperature of the cryogenic probe tip to at least −196° C. and especially −200° C. or lower, within a very short period of time, preferably within one minute and especially within 30 seconds after initiation of the delivery of the sub-cooled $LN_2$ from the refrigeration system. The $LN_2$ may be supplied under relatively low pressure, such as 20 to 100 psi, preferably 40 to 60 psi.

One system for generating sub-cooled cryogenic refrigerant which may be conveniently housed in a mobile manifold unit or in a mobile cart storage and supply unit, is described in the aforementioned application Ser. No. 07/588,329, the disclosure of which is incorporated in its entirety herein by reference thereto.

The mobile cart may include one or more storage vessels for liquid nitrogen to be used as the cryogenic liquid refrigerant for the cryoprobe and also for use as the refrigerant for the refrigeration system.

According to a preferred embodiment of this invention such storage vessels, e.g. Dewars, may be arranged vertically relative to one another and connected through a series of valves in a manner so as to allow one dewar to act as an $LN_2$ retrieval vessel for collecting any $LN_2$ recovered from the cryoprobe during a surgical procedure. The vertical arrangement is another advantage of the present invention in that it eliminates the need to use high pressure to transfer $LN_2$ from a retrieval tank to a supply tank as in the aforementioned application. Instead, in the present arrangement, gravity flow can be used to facilitate the transfer of recovered $LN_2$ to the $LN_2$ supply tank from the retrieval tank. Such an arrangement allows for use of lower pressure to transfer $LN_2$.

At least one of the vertically arranged dewars may contain a slush chamber therein for sub-cooling the liquid cryogen to a temperature below its normal boiling point, for example at or near the triple point at which temperature liquid and solid nitrogen are in equilibrium and form a thickened mixture known as "nitrogen slush" in which liquid and solid nitrogen coexist. An $LN_2$ supply dewar, for example, may contain a slush chamber. Such an arrangement provides a more compact system for sub-cooling liquid cryogen for use with the cryoprobe instrument. Other refrigeration units for sub-cooling the liquid cryogen, especially liquid nitrogen are known in the art and can be used in this invention, for example, U.S. Pat. Nos. 3,455,117, 4,620,962, 4,296,610, 4,715,187 and 4,716,738, the disclosures of which are incorporated herein by reference thereto. In any case, whichever refrigeration system is used, one of the prominent advantages of the cryoprobe of this invention is that due to its more efficient utilization of the sub-cooled cryogenic refrigerant, and the very substantially reduced time required to achieve operating temperatures, the volume of the $LN_2$ storage dewar can generally be substantially reduced for any given operation, thereby making the overall system more compact and less expensive.

An important advantage of the very low probe tip temperatures made possible by the use of sub-cooled $LN_2$ as the probe refrigerant is the ability to reduce the diameter of the probe tip while maintaining high freezing capacity. For example, according to the present invention, a probe tip outer diameter as small as about 1 or 1.5 to 3 millimeters can be used effectively for freezing much larger areas of tissue than for conventional cryoprobes of the same or larger diameter. Of course, larger probe tips can also be used, for example, up to about 10 millimeters.

The cryoprobe instrument of the present invention includes a body or handle portion and a probe shaft which is the operative portion and includes the freezing zone and closed end probe tip which come into contact with the tissue to be treated. Each of the body portion and probe shaft have an outer shell or casing formed from hollow tubing (all tubing used in the cryoprobe is generally and preferably of cylindrical cross-section). The outer shell may be a single piece of constant diameter, as in the probe of the aforementioned Rubinsky, et al. application and other conventional cryoprobes, and similarly the refrigerant supply tube and refrigerant exhaust tube which extend through the body portion and probe shaft may be formed from concentric tubes of constant diameter throughout their length.

However, in accordance with the preferred embodiment of the cryoprobe instrument of this invention the outer casing for the probe shaft has a smaller diameter than the outer casing of the body portion. Similarly, the concentric cryogen supply tube and exhaust tube have larger diameters in the body portion than in the probe shaft. Accordingly, the larger diameter sections provide less impedance to the free flow of the liquid cryogen from the cryogen supply vessel and connecting tubing through the cryogen supply tube until the reduced diameter portion in the probe shaft, and similarly, less impedance to flow and opportunity for boiling of the refrigerant flowing from the closed probe tip end through the exhaust channel out of the cryoprobe instrument, either to be vented into the atmosphere, or preferably, returned to a collection vessel available for reuse. Even more preferably, the exhaust tube includes an enlarged portion at the proximal or open end of the probe body/handle portion.

The sections of tubing of different diameter can be constructed of a single piece or of separate tubing sections welded together with fluid tight seals.

The space between the outer shell casing and the refrigerant exhaust tube is filled with thermal insulation to prevent the shell, except at the freezing zone at the distal end of the probe shaft, from attaining freezing temperature, as is well known in the art. The thermal insulation may be provided by air or other gas, or by solid thermal insulating material. The preferred thermal insulation, however, is a vacuum, which may be an active vacuum as in the Rubinsky, et al. application, but generally is a fixed, permanent vacuum. Furthermore, in accordance with a preferred embodiment a gas adsorbent, such as activated charcoal or zeolite, for example, may be included within the vacuum chamber to further lower the pressure by adsorbing any gases not evacuated from the chamber when the chamber is sealed, or any gas which may leak into the vacuum chamber. The adsorbent is used in the form of a powder and is preferably adhered to the inner walls of the vacuum chamber using adhesive, e.g. epoxy, or by fusing or sintering. Having the adsorbent powder adhere to the walls is advantages to avoid clumping, thereby maximizing available surface area available for adsorbing any residual gases. In practice, vacuum as low as about $10^{-7}$ mmHg have been formed. In the preferred embodiment, the larger and smaller diameter sections of the supply tube coincide with and are concentrically located within the similarly larger and smaller diameter sections of the exhaust flow tube as well as the larger and smaller diameter sections of the outer casing.

As may readily by appreciated, especially for the preferred cryoprobe instruments of very small probe shaft diameters, e.g. up to about 6 mm, especially up to about 4 mm, such as 1.0 or 1.5 to 3 mm, there is only a very small clearance between the refrigerant supply tube outer wall and the exhaust tube inner wall and between the exhaust tube outer wall and the vacuum chamber wall or inner wall of the outer shell. Accordingly, it is within the scope of the invention to provide a protective insulating tape, such as Teflon tape, for example, wrapped around the exhaust flow tube so as prevent contact between the exhaust tube and outer shell. Such insulation serves to prevent the formation of ice crystals on the outside of the shell casing.

The open end of the body portion of the cryoprobe instrument is connected to the refrigerant supply vessel and associated delivery tubing or conduits, and any necessary electrical supply lines, via a delivery connector, usually through appropriate coupling means, such as screw threads. Thus, the refrigerant $LN_2$ delivery connector may include at one end thereof a means for fluid tightly receiving one end of the external (to the cryoprobe instrument) $LN_2$ supply and return tubes and electrical wiring and at the opposite end means for fluid tightly receiving the open end or base of the probe body, e.g. a male threaded portion which engages with female threads of the probe body.

Solid metal electrical contacts or male and female electrical connectors or thermocouple pins may also be provided on each of the mutually mating ends of the delivery connector and probe base such that when the parts are assembled the metal electrical contacts or male and female connectors are in electrical contact with each other to complete the electrical wiring circuit to a thermocouple in the probe tip. In a preferred embodiment, a thermocouple joint is formed at the end of the $LN_2$ supply tube and thermocouple wires run through the space between the $LN_2$ supply tube and the exhaust flow tube and connect to the thermocouple pins.

The delivery connector may be molded from Teflon or similar self-lubricating, low friction plastic or resin material with relatively low heat transfer coefficient.

When the probe body is connected to the $LN_2$ delivery connector the probe's internal $LN_2$ supply tube will extend into or through the delivery connector so that its inlet end may be connected in fluid flow communication with the $LN_2$ supply. The probe's exhaust flow tube may terminate at the open end of the probe's base and communicate with an enlarged chamber of the delivery connector such that exhausted refrigerant from the probe tip will flow through the exhaust flow tube and enlarged chamber and will be in fluid flow communication with a cylindrical bore extending through and located in the delivery connector spaced in axial alignment with the longitudinal axis of the probe. A second cylindrical bore extends through the delivery connector and is in axial alignment with the longitudinal axis of the probe. The second cylindrical bore has substantially the same diameter as the outside diameter of the $LN_2$ supply tube so that a fluid tight compression fit is formed between the periphery of the tube and the cylindrical bore.

The most prominent and distinguishing feature of the cryoprobe instrument of the present invention is an internal venting system which provides for the free flow of $LN_2$ through the supply tube and also maintains the exhaust refrigerant in the exhaust flow tube at a lower temperature than in conventional cryoprobes, thereby maintaining a lower temperature of $LN_2$ in the supply tube, ultimately resulting in lower temperatures, such as, for example, $-206°$ C. at the probe tip. Moreover, the internal venting system of the present invention allows the probe tip to achieve lower temperatures significantly faster than conventional cryoprobes including the improved probe of the aforementioned Rubinsky, et al. application.

The internal venting system of the present invention is provided along the $LN_2$ supply tube. The $LN_2$ supply tube is provided with a series of small holes, which are sufficiently small as compared to the inside diameter of the $LN_2$ supply tube to prevent the free flow of $LN_2$ from the $LN_2$ supply line except at its outlet end, but large enough to allow any gas within the $LN_2$ supply line to escape through the holes into the surrounding exhaust flow tube as well as some liquid leakage into the exhaust tube. The vent holes provide three major functions in the cryoprobe instrument: 1) to maintain a high flow rate of $LN_2$ from the $LN_2$ inlet to the probe tip by venting any nitrogen or other gas present in or formed in the external $LN_2$ tube before the gas can impede the free flow of $LN_2$ through the probe's $LN_2$ supply tube, 2) to vent gas along the supply tube which may be formed by counter-current heat exchange between the exhaust refrigerant and the colder supply $LN_2$ and 3) to decrease the extent of the counter-current heat exchange by venting some $LN_2$ drops through the holes into the returning path of the exhaust refrigerant including any gas, thereby cooling or reliquefying the exhaust gas. A probable secondary effect of the vent holes is the additional cooling by Joules-Thompson phenomena which occurs when LN$_2$ in the supply tube is vented through the small vent holes into the exhaust flow tube. The resulting lower temperature of the exhaust refrigerant may thus serve to further decrease the formation of gas in the supply tube.

The internal venting system of the present invention may include an enlarged chamber at the probe base in communication with the exhaust flow tube. This enlarged chamber facilitates the flow of the returning exhaust refrigerant. In a most preferred embodiment, a hole is provided in the supply tube in a region surrounded by the enlarged chamber of the probe base and delivery connector. This hole is generally larger than any downstream vent holes, for example, about 0.008 to 0.050 inches, preferably about 0.01 to 0.040 inches, e.g. 0.030 to 0.035 or 0.038 inches, for a supply tube having an inner diameter in the range of from about 0.045 to 0.080 inches. The effect of this rearward-most hole is to shorten the time required to cool the probe tip by rapidly venting any gas present in, or formed in, the refrigerant delivery tube and LN$_2$ supply tube at the initiation of operation of the probe when the system has the highest heat load.

The cryogenic probe of the invention is also advantageously designed to have a larger diameter supply and exhaust flow tube in the upstream (i.e. proximal) region of the instrument body relative to the probe tip than in the downstream or distal region, e.g. the probe shaft. This widening of the exhaust flow and LN$_2$ supply tubes decreases flow resistance of LN$_2$ and returning liquid or gaseous refrigerant. Smaller diameter tubes are used in the distal portion of the instrument that are actually required for surgery, such as the freezing zone of the probe tip and an upstream region from the probe tip constituting the remainder of the probe shaft.

The size of the downstream ventilation holes is also an important feature in the internal venting system. The diameter of the holes may vary depending on the outer diameter of the LN$_2$ supply tube as well as the location of the hole(s), but in all cases the vent holes are smaller than the inner diameter of the LN$_2$ supply tube. For example, the ventilation holes located along the supply tube may have an outer diameter of from about 1/10 to 8/10 the inner diameter of the supply tube at the probe tip end. According to a most preferred embodiment of the invention, the downstream ventilation holes have a diameter less than that of the rearward-most hole and in the range of from about 0.005 to about 0.040 inch, preferably 0.008 to 0.030 inch.

The rearward-most ventilation hole of the supply tube surrounded by the enlarged chamber at the upstream end of the exhaust flow tube preferably has a larger diameter than that of the downstream ventilation holes located longitudinally along the supply tube, for example, about 1.5 to 2.5 times larger, such as twice as large in diameter.

The location of the ventilation holes relative to one another along the supply tube may have an effect on the efficiency of gas ventilation and exhaust gas cooling. In a most preferred embodiment of the invention, the holes are spaced equidistant from one another, however, equidistant spacing is not essential. The holes may be formed in any region of the supply tube, i.e. in the narrowest diameter region located within the probe shaft, in an intermediate region of the supply tube having a larger diameter, and in the proximal upstream region of the supply tube, which is surrounded by the enlarged chamber of the delivery connector/exhaust flow tube. Preferably in addition to the large hole communicating with the enlarged chamber one or two vent holes are included in each of the small diameter and intermediate or large diameter sections of the LN$_2$ supply tube. In a preferred embodiment, a single hole having a diameter of about 15-25 mil (0.015 to 0.025 inch) is located in the proximal region of the supply tube and two smaller holes having diameters in the range of about 5 to about 14 mil are located in each of the narrowest diameter section and larger diameter section intermediate the proximal end and the narrowest diameter section. The number of venting holes may vary depending on the length of the cryoprobe instrument, but generally from 2 to 8, preferably 4 to 6, such as 5 vent holes in total, will be sufficient.

An example of a cryosurgical instrument according to the invention is illustrated in FIG. 1. It is understood that the invention is not intended to be limited to the exact embodiments of the example, as many variations of the invention can be made.

Referring to FIG. 1, an embodiment of the cryoprobe instrument will be described. The cryoprobe instrument is shown generally at I and the LN$_2$ delivery connector is shown generally at II.

Figure 2:
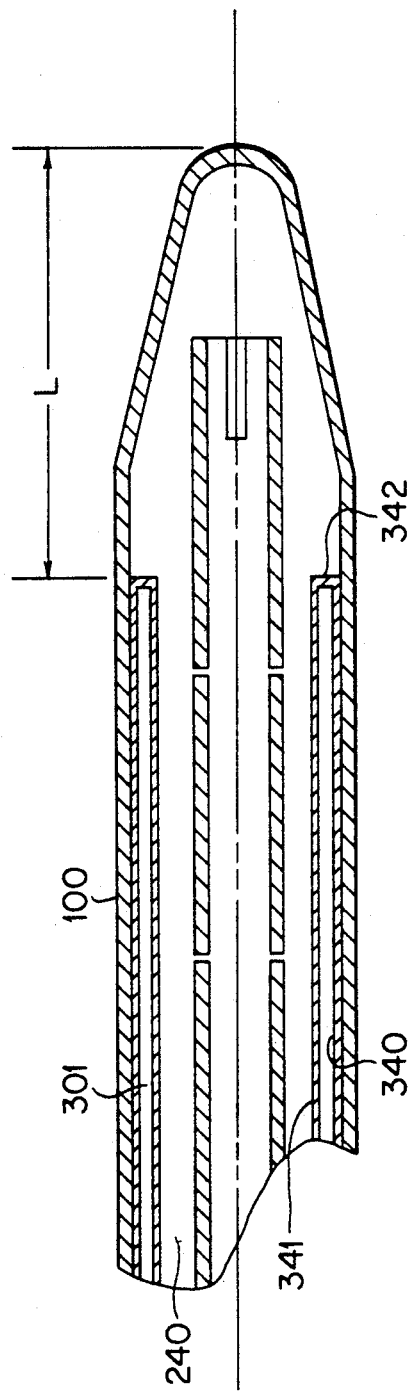
FIG. 2 is a sectional side view of an alternative embodiment of a portion of the cryosurgical probe tip including a movable vacuum chamber and adjustable freezing zone.

The outer shell or casing of the probe is shown generally at 10 and includes a large diameter upstream body portion 11, fluid tightly connected, e.g. by welding, to intermediate portion 12, which, in turn, is fluid tightly welded to probe shaft 13. Probe shaft 13 includes a closed end or tip 20 which includes the freeze zone 15 located upstream of vacuum insulation chamber 30. In the embodiment shown in FIG. 1 the freezing zone is of fixed predetermined length with end wall 31 of vacuum chamber 30 being welded fluid tightly to the inner wall of probe shaft 13. However, as shown in FIG. 2 it is also within the scope of the invention to provide a movable vacuum chamber 30' to adjust the length L of the freeze zone. For example, whereas in the embodiment of FIG. 1 only three concentric tubes are used to provide the vacuum chamber, LN$_2$ supply tube and refrigerant exhaust channel, it is possible to provide a fourth concentric tube 340 in sliding contact with the outer casing 100, which, together with the intermediate concentric tube 341 forming the outer wall of the refrigerant exhaust channel 240 to which the end 342 of the fourth tube is tightly welded, forms the thermal vacuum insulation chamber 301. Then, by moving the casing 100 relative to the end 342 of the vacuum chamber, and forming a fluid tight seal between the casing and the vacuum chamber, the length L of the freezing zone may be increased or decreased, depending on, for example, the size and depth of the solid tumor being treated. The fluid tight seal may be formed, for example, by crimping the casing near the end of the vacuum chamber, or by an appropriate, low temperature sealant provided between the outer casing and the "contacting" wall of the vacuum chamber.

The LN$_2$ supply tube 22 includes large diameter upstream section 25 and reduced diameter section 28 welded together at 26 which is shown located near the downstream end of intermediate body section 12. The reduced diameter section 28 extends through most of probe shaft 13 extending beyond the end 31 of the vacuum chamber which is coextensive with the inlet 27 of the exhaust refrigerant flow channel or passageway. The outlet end 23 of supply tube section 28 may be slotted (as shown in FIG. 2) to facilitate flow of the LN$_2$ to the closed end of the probe tip and freezing zone.

The exhaust flow passageway or channel 24 for removing used LN$_2$ from the freeze zone is defined, on the one hand, by the outer surface of supply tube sections 28 and 25, and on the other, the inner surface of the smaller diameter exhaust flow tube 34 and larger diameter exhaust flow tube section 32 and continuing into the enlarged hollow chamber 17 at the open end 18 of the probe. Tubes 32 and 34 are concentric with LN$_2$ supply tube sections 25 and 28 and together with inner surface of probe casing tubing 11, 12 and 13 and end wall 18, rear wall 19 and wall section 14 defining chamber 17, define the vacuum insulation chamber 30. Solid adsorbent particles 37, such as zeolite particles, are adhered to the inner surfaces of the walls of the vacuum chamber in the body portion 11 and intermediate portion 12 to help reduce the amount of gas in the vacuum chamber. Also, insulation tape 38 is shown wrapped around the outer surface of exhaust flow tube section 34. Tape 38 serves to prevent point contact between tube section 34 and concentric probe shaft 13 and therefore inhibits formation of ice crystals on the outer surface of the probe shaft during use. Although shown only at the proximal or upstream end of tube 34, protective insulative tape 38 may be provided over substantially the entire length of tube 34.

LN$_2$ supply tube 22 is shown with 5 vent holes, including rearwardmost vent hole 29, intermediate section vent holes 29a, 29b and forward vent holes 29c and 29d. Vent hole 29 is formed with a larger diameter than vent holes 29a-d and when supply tube 22 is fully inserted into the probe as shown in the figure vent hole 29 is located in enlarged chamber 17. More or fewer vent holes and different locations of the vent holes may also be used. For example, while all of the vent holes are shown as formed in a straight line coinciding with the longitudinal axis of the probe, the holes may be staggered or spiraled around the circumference of the supply tube sections. Generally, and preferably the holes extend through only one wall around the circumference, however, the holes may also be drilled through both circumferential walls, e.g. spaced 180°.

In practice, the probe may be assembled by providing probe shaft 13 as an open ended tube to provide access to the end 31 of exhaust flow tube section 34 which end 31 is welded to the inner surface of the probe shaft after vacuum chamber 30 is evacuated. Alternatively, vacuum chamber 30 may be evacuated through end wall 18 or at any intermediate location using techniques well known in the art. After exhaust tube end 31 is fluid tightly welded to probe shaft tube 13 the closed tip end 20 is welded to the probe shaft tube 13 and the weld is appropriately polished to provide a smooth outer surface. It should be noted that in the previously described alternative embodiment utilizing four concentric tubes, with the vacuum chamber in sliding contact with the probe shaft tube, the end of the vacuum chamber will not be welded to the inner surface of the probe shaft as in the embodiment illustrated in FIG. 1.

The liquid nitrogen delivery connector II is shown as a cylindrical body 40 formed from low friction, low temperature insulative, low expansion coefficient material, such as Teflon. The enlarged diameter section 41 may have a slightly larger diameter than that of body section 11. Reduced diameter section 43 includes male threads 42 which threadingly and sealingly engage with female threads 16 o wall section 14 of chamber 17.

Additional sealing means such as an O-ring may also be provided to ensure a fluid tight seal between the connector and probe.

Connector 40 is provided with generally cylindrical through bores. Bore 44 is located on the longitudinal axis of the probe and is of substantially the same or slightly smaller diameter than the outer diameter of LN$_2$ supply tube section 25 to fluid tightly receive the LN$_2$ supply tube section 25. As shown in FIG. 1, the inlet end 21 of LN$_2$ supply tube 22 extends beyond the delivery connector for attachment to an LN$_2$ delivery line (not shown) and the outlet end 23 extends into freeze zone 15 spaced from the closed tip end 20. Connector body 40 also includes the thin annular section 48 to further define chamber 17. A second cylindrical through bore 4 is provided parallel to and axially spaced from bore 44. Steel tube 50 is tightly fitted in bore 45 and forms part of the exhaust refrigerant flow passageway in communication with the enlarged chamber 17 and flow channel 24. Tube 50 will be connected to suitable tubing to return the used refrigerant to a retrieval vessel or to atmosphere. Appropriate connectors and tubing/hoses for connecting to tube 50, tube 22 and thermocouple pins are shown, for example, in the aforementioned Rubinsky, et al. application. A third through bore 46 receives a thermocouple pin 52 which in conjunction with a second thermocouple pin (not shown) and thermocouple wiring and thermocouples (not shown) located, for example, at the outlet 23 of LN$_2$ supply tube, and/or at the probe shaft wall in freezing zone section 15, help monitor the tip temperature.

A cryoprobe instrument has been prepared as shown in FIG. 1. The outer shell 10 was formed using a 3.25 inch (82.55 mm) long, 1 inch (25.4 mm) diameter (O.D.) standard wall stainless steel tube for body portion 11, ⅝ inch (15.9 mm) (O.D.), 2.25 inch (57.2 mm) long standard wall stainless steel tube for intermediate section 12 and 7.25 inch (184 mm), 3 millimeter O.D. thin wall stainless steel tube for the probe shaft 13. Exhaust flow tube section 32 is formed from thin wall stainless steel tube 10 TW (0.187 inch O.D.) and small diameter section 34 was formed from stainless steel tube with an outside diameter of 0.082 inch and a wall thickness of 0.008 inch. The LN$_2$ supply tube 22 includes large diameter section 25 formed from 12 TW (O.D.=0.108–0.110 inch, wall thickness=0.009 inch) stainless steel tube and reduced diameter section 28 formed from 19 XTW (O.D.=0.0415–0.0425 inch, wall thickness=0.0035 inch) stainless steel tube. Vent hole 29 is drilled with a single filament wire drill to a diameter of 0.020 inch (0.508 mm) located in vacuum chamber 17. Holes 29a-d are drilled to a diameter of 0.010 inch (0.254 mm). Hollow chamber 17 is formed from a ⅝ inch threaded (NPT) cap. Vacuum chamber 30, with the assistance of zeolite particles 37 is evacuated to $10^{-7}$ mmHg. Teflon tape was wrapped around tube 34.

Using the structure described above, with sub-cooled liquid nitrogen at approximately −200° C. supplied at a pressure of 40 to 60 psi to the inlet of LN$_2$ supply tube 22 at a flow rate of approximately 0.25 liters per minute, the temperature at the probe tip can be reduced to and maintained at approximately −200° C. Moreover, a temperature of −206° C. can be achieved in as little time as 30 seconds. In comparison, a conventional cryoprobe having a probe tip diameter of 3 mm but without vent holes, cannot achieve temperatures as low as −196° C.

The structure described above is capable of forming an ice ball as large as 40 mm in diameter within 20 minutes of operation. Furthermore, for a cryosurgical probe with the same dimensions of the cryogen supply tube and cryogen return tube but with a probe shaft diameter of 6 millimeters an ice ball as large as 70 to 75 millimeters (approximately 3 inches) can be obtained. With currently available cryoprobes a probe shaft diameter of at least 9 millimeters is required to obtain an ice ball of near these dimensions. The length of the ice ball varies with the length of the probe tip.

A specific embodiment of the invention has been described in detail, however, it should be understood that the present invention may be varied and modified without departing from the scope of the invention.

What is claimed is:

1. In a cryoprobe instrument including a probe casing having a closed end including a freezing zone for freezing live tissue and an open end, a cryogenic refrigerant supply tube having a supply tube inlet for receiving liquid cryogenic refrigerant at the open end and a supply tube outlet for delivering the liquid cryogenic refrigerant to the freezing zone at the closed end, a cryogenic refrigerant exhaust channel surrounding the supply tube for transporting the used refrigerant from the closed end towards the open end, said exhaust channel having an exhaust channel inlet, and thermal insulation for insulating the side wall of the probe casing from the exhaust channel inlet to the open end, the improvement comprising at least one vent hole in the supply tube upstream of said freezing zone and located between the exhaust channel inlet and the supply tube inlet and in flow communication with the thermally insulated exhaust channel thereby enabling during operation of the cryoprobe instrument gas formed or present in the supply tube to be vented to the exhaust channel.

2. The improved cryoprobe instrument of claim 1 wherein a plurality of vent holes are provided, upstream of the freezing zone between the exhaust channel inlet and supply tube inlet, longitudinally spaced along the supply tube.

3. The improved cryoprobe instrument of claim 2 wherein the vent holes have diameters in the range of from about 0.005 to 0.050 inches.

4. The improved cryoprobe instrument of claim 2 wherein the vent holes have diameters in the range of from about 0.008 to 0.025 inches.

5. The improved cryoprobe instrument of claim 2 comprising from 2 to 8 vent holes wherein the rearwardmost vent hole has a diameter of from about 0.008 to 0.030 inches and wherein, each of the remaining vent holes is of smaller diameter in the range of from about 0.005 to 0.015 inches.

6. The improved cryoprobe instrument of claim 5 wherein the probe casing comprises an enlarged diameter handle portion at the open end thereof remote from the closed end, and a smaller diameter shaft portion including the closed end thereof.

7. The improved cryoprobe instrument of claim 6 wherein the shaft portion has a diameter of from about 1.5 to 3 millimeters.

8. The improved cryoprobe instrument of claim 6 wherein the exhaust channel comprises an enlarged diameter portion defining an exhaust chamber at the open end of the casing, a small diameter portion in the shaft portion and an intermediate diameter portion connecting the enlarged diameter portion to the small diameter portion.

9. The improved cryoprobe instrument of claim 8 wherein the supply tube comprises a small diameter portion in the shaft portion of the casing and a larger diameter portion extending from the small diameter portion to beyond the open end of the casing, thereby providing a larger annular exhaust flow passageway in the handle portion than in the probe shaft portion.

10. The improved cryoprobe instrument of claim 1 which further comprises a sealed tubular vacuum chamber, the outer wall of which is in sliding contact engagement with the inner wall of the probe casing and the inner wall of which defines the outside wall of the exhaust channel, whereby sliding movement of the vacuum chamber relative to the closed end of the probe tip varies the length of the freezing zone of the cryoprobe instrument which during use will provide freezing of tissue in contact therewith.

11. A cyrosurgical instrument which comprises a hollow probe tip having a closed end forming a freezing zone for freezing live tissue, a first inlet for receiving cryogenic liquid refrigerant and a first outlet for removing cryogenic refrigerant, a refrigerant supply tube for transporting cryogenic liquid refrigerant from the first inlet to the probe tip, said supply tube having at least one longitudinally located ventilation hole of a size in the range of from about 0.005 to 0.050 inches, an exhaust flow tube providing a flow passageway for transporting refrigerant from the freezing zone to the first outlet, wherein the supply tube and exhaust flow tube are arranged as concentric inner and outer tubes, with the supply tube forming the inner tube and extending beyond the outer tube in the freezing zone, and a thermal insulation chamber surrounding said concentric tubes and extending to the freezing zone, whereby the at least one ventilation hole is located upstream of said freezing zone and allows ventilation of gas formed in the supply tube so as to maintain a high flow rate of refrigerant through the supply tube and to decrease the extent of counter-current heat exchange between the cryogenic refrigerant in the supply tube and the exhaust flow tube by allowing refrigerant to vent to the exhaust flow tube and thereby cool the cryogenic refrigerant flowing through the exhaust tube.

12. The cryosurgical instrument of claim 11 wherein the supply tube comprises an upstream area at the first inlet and a downstream area extending to the probe tip wherein said upstream area has a larger diameter than that of the downstream area.

13. The cryosurgical instrument of claim 11 wherein the exhaust flow passageway comprises an upstream section extending to said freezing zone, a first downstream section having an outer diameter larger than that of the upstream section and a second downstream section extending to the first outlet; wherein the second downstream section is an enlarged chamber having a diameter larger than that of the first downstream section and said first downstream section is located between the upstream section and the second downstream section.

14. The cryosurgical instrument of claim 13 wherein a first least one ventilation hole of the supply tube is located in an area of the supply tube surrounded by the enlarged chamber of the exhaust flow passageway.

15. The cryosurgical instrument of claim 14 wherein the supply tube is provided with at least one vent hole located longitudinally downstream from said first ventilation hole and upstream of said freezing zone.

16. The cryosurgical instrument of claim 14 wherein the first at least one ventilation hole has a diameter in the range of about 0.010 inch to about 0.035 inch.

17. The cryosurgical instrument of claim 14 comprising from 2 to 8 vent holes wherein the first at least one ventilation hole located in the area of the supply tube surrounded by the enlarged chamber has a diameter of from about 0.008 to 0.030 inches and wherein each of the remaining vent holes is of smaller diameter in a range of from about 0.005 to 0.015 inches.

18. The cryosurgical instrument of claim 17 wherein the portion of the hollow probe tip which includes the freezing zone has an outer diameter of about 3 mm.

19. The cryosurgical instrument of claim 11 wherein a portion of the exhaust flow tube is insulated with protective tape, whereby the exhaust tube is physically separated and thermally insulated from the wall of the hollow probe tip and formation of ice crystals on the outside surface of said cryosurgical instrument is prevented.

20. The cryosurgical instrument of claim 11 wherein the thermal insulation chamber comprises a vacuum chamber.

21. The cryosurgical instrument of claim 20 wherein the vacuum chamber comprises an inner surface having adhered thereto a plurality of gas absorbent particles.

22. The cryosurgical instrument of claim 21 wherein the absorbent particles comprise zeolite particles.

23. The cryosurgical instrument of claim 11 wherein the portion of the hollow probe tip which includes the freezing zone has an outer diameter in the range of from about 1.5 to about 3 mm.

24. A method for producing sub-freezing temperatures sufficiently low to destroy living tissue by supplying sub-cooled cryogenic liquid through an insulated passageway to a closed tip of highly temperature conducive material at the end of the passageway, said method comprising providing a stream of sub-cooled cryogenic liquid refrigerant from a supply thereof through a first flow passageway having an outlet terminating in the vicinity of but spaced from the closed tip, said flow passageway including a plurality of vent holes along the length thereof, causing the cryogenic refrigerant to flow in counter-current flow from the closed tip in an annular second flow passageway surrounding said first flow passageway, and providing thermal insulation of the refrigerant flowing through the second flow passageway and extending longitudinally beyond said plurality of vent holes, whereby gas initially present in the first flow passageway is vented through at least one vent hole into the second flow passageway, and any vaporized liquid cryogen flowing through the first passageway can be vented into the second flow passageway, said plurality of vent holes each having a diameter in the range of from about 0.005 to 0.050 inches and smaller than the diameter of the outlet of the first flow passageway, said vent hole diameter being sufficient to allow liquid to be vented from said first passageway to said second passageway, whereby bubbling of the cryogenic liquid in the first flow passageway which would impede flow of liquid therethrough is effectively inhibited, and the temperature differential between the liquid cryogen flowing through the first flow passageway and the counter-current flowing refrigerant in the second flow passageway is reduced.

* * * * *